US009133419B2

(12) United States Patent
Wilker et al.

(10) Patent No.: US 9,133,419 B2

(45) Date of Patent: Sep. 15, 2015

(54) REDUCTION OR REMOVAL OF CHLORHEXIDINE AND/OR AVOBENZONE FROM FABRIC MATERIALS

(71) Applicant: Proteus Solutions, LLC, Cincinnati, OH (US)

(72) Inventors: Christopher Wilker, Cincinnati, OH (US); Scott D. McCormick, Cincinnati, OH (US); James Michael Lyle, McEwen, TN (US)

(73) Assignee: Washing Systems, LLC (EAW), Cincinnati, OH (US)

( * ) Notice: Subject to any disclaimer, the term of this patent is extended or adjusted under 35 U.S.C. 154(b) by 417 days.

(21) Appl. No.: 13/716,980

(22) Filed: Dec. 17, 2012

(65) Prior Publication Data

US 2014/0165294 A1 Jun. 19, 2014

(51) Int. Cl.

| | |
|---|---|
| ***A61K 6/02*** | (2006.01) |
| ***B29D 11/00*** | (2006.01) |
| ***C08F 2/46*** | (2006.01) |
| ***C08G 61/04*** | (2006.01) |
| ***C11D 3/04*** | (2006.01) |
| ***C11D 11/00*** | (2006.01) |

(52) U.S. Cl.

CPC ............ *C11D 3/042* (2013.01); *C11D 11/0017* (2013.01); *C11D 11/0064* (2013.01)

(58) Field of Classification Search

CPC ............. C11D 3/0042; C11D 11/0017; C11D 11/0064

USPC ........... 522/179, 178, 1; 520/1; 510/276, 109, 510/108, 8, 513; 252/175, 387, 380

See application file for complete search history.

(56) References Cited

U.S. PATENT DOCUMENTS

| | | | | |
|---|---|---|---|---|
| 3,142,165 | A * | 7/1964 | McMillan | 68/17 A |
| 3,328,308 | A | 6/1967 | Mackenzie | |
| 4,963,158 | A | 10/1990 | Beaujean et al. | |
| 5,057,238 | A | 10/1991 | Broze et al. | |
| 5,112,358 | A | 5/1992 | Deal, III | |
| 5,645,608 | A | 7/1997 | Cooper et al. | |
| 6,277,153 | B1 | 8/2001 | Van Kouwen et al. | |
| 8,268,769 | B2 | 9/2012 | Enselberg | |
| 2008/0045431 | A1 * | 2/2008 | Corradini | 510/362 |
| 2012/0066840 | A1 * | 3/2012 | Man et al. | 8/137 |
| 2012/0071384 | A1 | 3/2012 | Christensen et al. | |
| 2013/0192006 | A1 | 8/2013 | Tinker et al. | |

* cited by examiner

*Primary Examiner* — Ling Choi

*Assistant Examiner* — Jessica E Whiteley

(74) *Attorney, Agent, or Firm* — Wood, Herron & Evans, LLP

(57) ABSTRACT

A method for removing chlorhexidine and/or avobenzone from fabric materials utilizes an acidic detergent composition including phosphoric acid and a surfactant in a flush cycle of a washing machine adapted to perform separate flush, wash, and bleaching cycles. The acidic detergent composition is present in the flush solution in a sufficient quantity to provide a pH less than about 5 and, advantageously, above about 2. The acidic detergent composition is advantageously substantially free of a chlorine-based oxidant.

10 Claims, 2 Drawing Sheets

REDUCTION OR REMOVAL OF CHLORHEXIDINE AND/OR AVOBENZONE FROM FABRIC MATERIALS

FIELD OF THE INVENTION

The present invention relates to reduction or removal of chlorhexidine and avobenzone from fabric materials, such as sheets, towels, gowns, robes, and other linens, and more particularly to methods and compositions for doing so.

BACKGROUND

In the institutional laundry field, such as for hospitals or hotels, the large scale, industrial washing machines process laundry in three general steps or cycles; a flush cycle, a wash cycle, and a bleaching cycle. The linens are run through a flush cycle (also referred to as a pre-wash or first wash cycle), where large dirt and loose components (such as debris and bodily waste) are removed from a load of linens as the flush solution is discharged from the washing machine. Then, the linens are run through a wash cycle, followed by a bleaching cycle. Rinse cycles may be interposed between the washing and bleaching cycles, and after the bleaching cycle. One such washing machine is known as an extractor. The extractor has one large tub into which the soiled linens are placed, and each cycle is then conducted in sequence using the same tub, with liquid introduced as necessary for each cycle, and the liquid used during the cycle removed before the next cycle begins. Another industrial washing machine type is a tunnel or continuous batch washer (CBW). In a CBW, linens pass from stage to stage of the tunnel where each cycle is conducted, typically with liquid from a subsequent stage. Thus, a first stage receives the soiled linen, liquid is introduced, which may be the remaining liquid from the next or subsequent stages, and the flush cycle conducted. The liquid from the flush stage, along with the heavy soil, is discharged, and the now flushed laundry is moved to the next stage(s) or cycle(s). This sequence continues through wash and bleach cycles, as well as any intervening or subsequent rinse cycles, until the cleaned linen load is available at the last stage. Thus, a first stage receives the soiled linen, liquid is introduced, which may be the remaining liquid from the next or subsequent stages and/or fresh water, and the flush cycle conducted.

While the foregoing types of industrial washing machines, and their operational processes are well entrenched in the institutional laundry field, certain stains have been found difficult, if not impossible, to avoid. Two particularly challenging stains arise from the use of chlorhexidine and avobenzone in healthcare and hospitality settings, respectively. Chlorhexidine is used extensively in the healthcare field in such products as Habiclens®, Savinox Plus®, Surgiprep-CHX™, Hibiscrub™, or Dexiden™. In a hospital or other healthcare setting, the chlorhexidine-containing products soak into various linen items used by patients and medical care givers, such as gowns, sheets, scrubs, and other similar linens. Avobenzone is used as a sunscreen and, so is similarly present in linens and robes after they have been used in hospitality facilities such as hotels and motels, for example. Chlorhexidine and avobenzone, when present, tend to stain the fabric materials with which they come into contact, and these stains are difficult to remove.

Typical laundry processes are considered insufficient to adequately deal with staining from chlorhexidine or avobenzone. Instead, the typical laundry process merely masks or fades the stain. That is not a desirable result.

SUMMARY

We have determined that chlorhexidine and avobenzone, when present, are typically becoming set or otherwise bound to the fibers of the fabric material during the flush cycle of the washing machine. In particular, the flush cycle is often conducted with liquid that contains high levels of free chlorine (e.g., from chloride-based oxidants such as bleach) and/or at a high basic pH. In the extractors, the flush liquid might simply be municipal water, which is often high in chlorine content. And in some cases, there is also a fair amount of iron in the water, which tends to further aggravate problems with avobenzone. The cost and expense of changing the flush process to avoid such chlorine-laden liquids is not seen as a good solution, because the water and/or other materials present in the wash, bleach, and/or rinsing processes can lead to the same result. In continuous batch washers, the chlorine employed in subsequent stages tends to be at high levels by the time that liquid is available for use in the initial flush stage of the machine. Some have suggested changes to the subsequent or downstream cycles or stages in order to minimize the addition of chlorine, but those changes are not considered to be desirable. In particular, the damage is often already done due to remaining chlorine in the flush stage and those changes are, in any event, costly.

Further, some have suggested replacing chlorine-based oxidants altogether, but the cost and expense of changing the laundry process to replace chlorine-based oxidants is not seen as a good solution. First, the non-chlorine-based oxidants are generally more expensive. But more importantly, non-chlorine-based oxidants, such as peroxides or peracids, do not remove chlorhexidine from the fabric material. Instead, peroxides and/or peracids react with chlorhexidine to form stains that, while not discernible under visible light, are visible under ultraviolet light.

We have determined that chlorhexidine and/or avobenzone need to be freed up from the fabric materials as part of the flush cycle in order to remove those chemicals before they can set in to the fibers. In that way, they are removed or at least reduced from the fabric materials. To that end, and in accordance with the principles of the present invention, we have discovered that conducting the flush cycle in the presence of an acidic detergent composition including phosphoric acid and a surfactant which, when mixed with the flush liquid provides a flush solution at a pH of less than about 5, results in freeing the chlorhexidine and/or the avobenzone otherwise present on or in the fabric materials. Advantageously, the flush solution may be at a pH of greater than about 2. The chlorhexidine and/or avobenzone to the extent freed from the fibers of the fabric materials can be carried away with the discharged flush solution, thus avoiding the staining and problems those chemicals otherwise normally present.

In accordance with one aspect of the present invention, a load of laundry is placed into a washing machine adapted to carry out separate flush, wash, and bleach cycles. Flush liquid and the acidic detergent composition are introduced into the machine for the flush cycle, and the flush cycle is conducted. During the flush cycle, the fabric materials are exposed to the flush solution thus created such that chlorhexidine and/or avobenzone on or in the fibers of the fabric materials can interact with the flush solution so as to be freed from the fabric materials. The flush solution is advantageously discharged during or after the flush cycle so as to carry away the freed chlorhexidine and/or avobenzone. In any event, the effect of the acidic detergent composition as part of the flush cycle reduces or eliminates staining from chlorhexidine and/or avobenzone, either in the flush cycle, or subsequent cycles of the washing machine.

While an acidic detergent composition considered beneficial for reduction or elimination of chlorhexidine and/or avobenzone during the flush cycle includes phosphoric acid and a surfactant, in accordance with another aspect of the present invention, the acidic detergent composition is advantageously substantially free of chlorine-based oxidants. In accordance with yet a further aspect of the present invention, the acidic detergent composition also includes a chelating agent. In accordance with a still further aspect of the present invention, the surfactant included in the acidic detergent may be an anionic surfactant. The surfactant may alternatively be any one of a disulfonated surfactant, a linear chain sulfonated surfactant, and a nonionic surfactant, or any two or all of a disulfonated surfactant, a linear chain sulfonated surfactant, and a nonionic surfactant.

By virtue of the foregoing, there is thus provided a method and a composition for reducing or eliminating chlorhexidine and/or avobenzone from fabric materials so as to avoid the irreversible staining normally occurring during the washing of fabric materials containing either of those chemicals. These and other advantages of the present invention shall be made apparent from the accompanying drawings and the description thereof.

BRIEF DESCRIPTION OF THE DRAWINGS

The accompanying drawings, which are incorporated in and constitute a part of this specification, illustrate an embodiment of the invention and together with the general description of the invention given above and the detailed description of the embodiments given below, serve to explain the principles of the present invention.

DETAILED DESCRIPTION OF EMBODIMENTS OF THE PRESENT INVENTION

Figure 1:
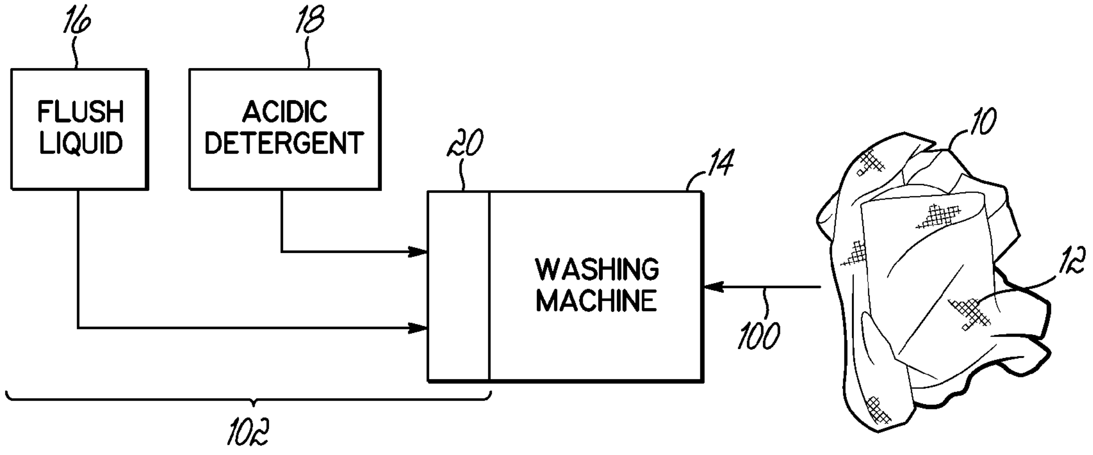
FIG. 1 is a diagrammatic depiction of soiled fabric materials undergoing a laundry process for purposes of explaining principles of the present invention.
Figure 2:
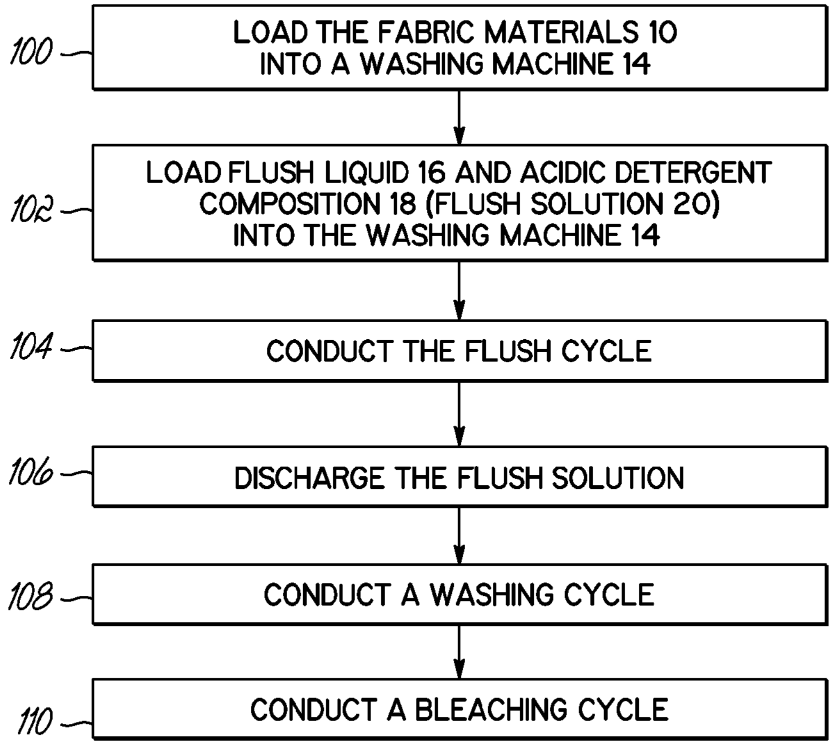
FIG. 2 is a flow chart depicting a method of cleaning fabric materials in accordance with principles of the present invention.

With reference to FIG. 1, fabric materials 10 may contain one or more items therein that include chlorhexidine and/or avobenzone as at 12 therein or thereon. In accordance with principles of the present invention, and with further reference to FIG. 2, in step 100, the fabric materials 10 are loaded into a washing machine 14 which is adapted to carry out separate flush, wash, and bleach cycles, as well as any desired rinse cycles, and in step 102 (which may comprise one step or multiple steps), flush liquid 16 and a quantity of acidic detergent composition 18 including phosphoric acid and a surfactant are loaded into the washing machine 14 to obtain a flush solution 20 at a pH of less than about 5, and advantageously above about 2. Steps 100 and 102 can take place in any order or can overlap, although step 100 may advantageously occur before step 102 begins. A flush cycle is conducted at step 104 (it will be appreciated that steps 102 and 104 may also be combined).

Figure 3:
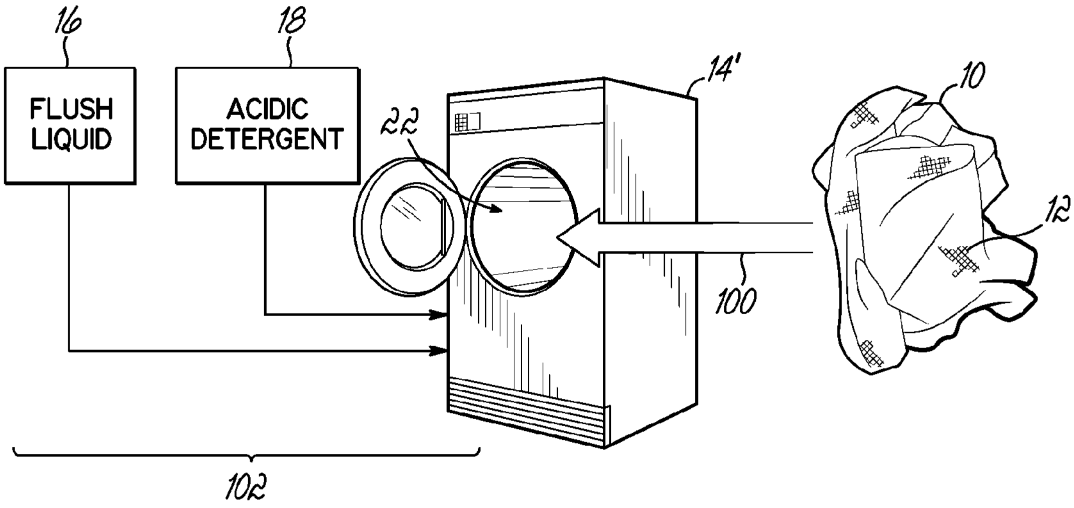
FIG. 3 is a diagrammatic depiction of a method of cleaning fabric materials using an extractor washer (EW), in accordance with an embodiment of the present invention.
Figure 4:
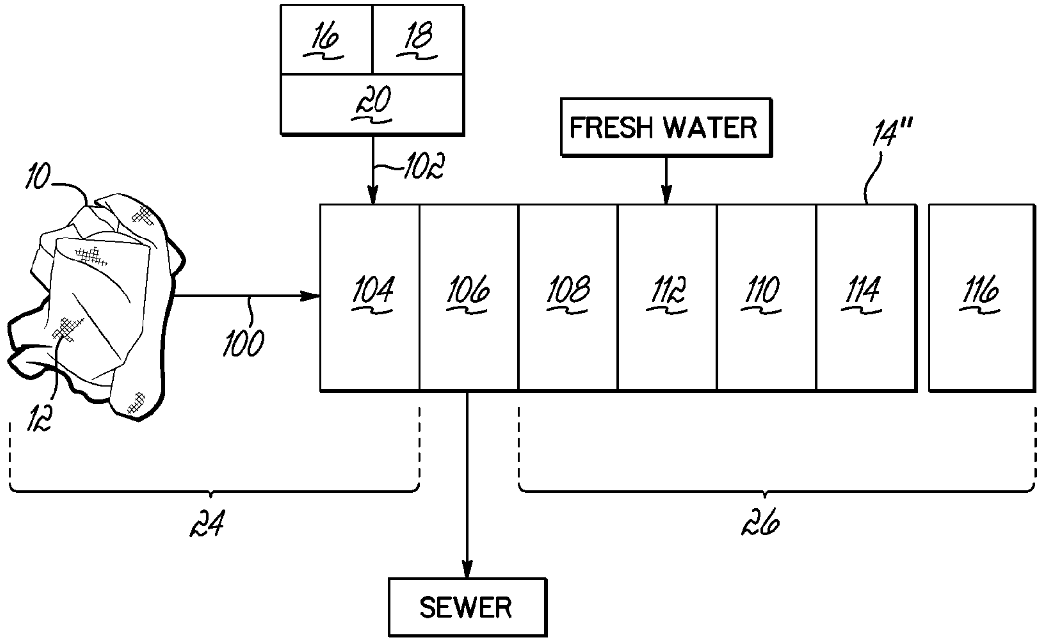
FIG. 4 is a diagrammatic depiction of a method of cleaning fabric materials using a continuous batch washer (CBW), in accordance with a principle of the present invention.

During the flush cycle, the fabric materials 10 are exposed to the flush solution 20 such that chlorhexidine and/or avobenzone on or in the fibers of the fabric materials 10 can interact with the flush solution 20 so as to be freed from the fabric materials 10. Depending on the specific application, the flush solution 20 may be utilized over a wide range of temperatures. For example, the flush solution 20 may be caused to be at a temperature in the range of about 15° C. to about 95° C. for or during the flush cycle, such as by heating the flush liquid 16 and/or the flush solution 20. More advantageously, the temperature may be in the range from about 45° C. to about 90° C., from about 50° C. to about 80° C., or from about 60° C. to about 75° C. At step 106, which is advantageously after completion of the flush cycle of step 104 but may be during or near the end thereof, the flush solution 20 is discharged from the washing machine 14 along with any debris and some or all of the chlorhexidine and/or avobenzone which had been associated with the fabric materials 10.

Where the washing machine 14 is an extractor 14' (FIG. 3), at step 100, fabric materials 10 and flush solution 20 are accommodated in tub 22. At steps 108 and 110, subsequent washing and bleaching cycles are conducted, along with intervening rinse cycles (not listed in FIG. 2) as may be desired, all within the same tub 22. Flush solution 20 is comprised of detergent composition 18 and flush liquid 16, where flush liquid 16 may be fresh water. Where washing machine 14 is a continuous batch washer 14" (FIG. 4), fabric materials 10 and flush solution 20 are accommodated in a first stage 24 thereof. The washing and bleaching cycles 108 and 110 (and intervening rinse cycles 112 and final sour/softening/anti-chlorination and press cycles 114, 116 as may be desired) typically occur in subsequent stages 26 thereof. Flush solution 20 is comprised of detergent composition 18 and flush liquid 16, where flush liquid 16 may be fresh water and/or liquid from downstream stages 26. A washing cycle, as at step 108, may be conducted with a detergent solution having a pH greater than 7, or may utilize a catholyte solution generated by electrochemical cells as described in U.S. patent application Ser. Nos. 13/568,491 or 13/568,506, both filed Aug. 7, 2012. A bleaching cycle, as at step 110, may be conducted with standard bleach solutions, or may utilize an anolyte solution generated by electrochemical cells as described in aforesaid U.S. patent application Ser. Nos. 13/568,491 or 13/568,506. Each stage or cycle shown in FIG. 4 may comprise one or more pockets.

After the flush cycle, or advantageously, after the flush solution 20 has been discharged, the fabric materials 10 are expected to have little or none of the chlorhexidine and/or avobenzone which may have been present before the flush cycle. As a consequence, the fabric materials 10 may be conducted through the washing and bleaching cycles (and any rinsing cycles that might be provided) with minimal risk of staining from such chemicals. The clean fabric materials 10 from the washing machine 14 are thus expected to have little, if any, stains from chlorhexidine and/or avobenzone.

Without being bound by any particularly theory, it is believed that the acidic detergent composition 18, which is a phosphoric acid-based detergent composition that includes a surfactant, increases the solubility of chlorhexidine in the flush liquid 16 and thereby facilitates removal of chlorhexidine present on fibers of the fabric material 10. Moreover, when used in a sufficient quantity to reduce the pH of the flush liquid 16 to less than 5, chlorhexidine that may have already bonded to the fibers can be hydrolytically cleaved therefrom.

This is particularly advantageous for fibers containing cotton cellulose, which are known to bind and/or react with chlorhexidine.

The addition of the acidic detergent composition 18 before or, as an elimination of, a high pH washing can also remove avobenzone before it is subjected to iron, which is often present in untreated tap water, and/or a basic pH (i.e., pH>7) of a typical laundry detergent. For example, formulations of the acidic detergent composition 18 comprising phosphoric acid can form a colorless, polyphosphate complex with iron, as an example, which inhibits the iron from reacting with avobenzone. This allows the acidic detergent composition 18 to facilitate the removal avobenzone from the fabric material 10 and prevent the avobenzone oxidation of the iron from depositing on the fabric material 10.

While an acidic detergent composition 18 considered beneficial for reduction or elimination of chlorhexidine and/or avobenzone during the flush cycle includes phosphoric acid and a surfactant, in accordance with another aspect of the present invention, the acidic detergent composition 18 advantageously is further substantially free of any chlorine-based oxidants (e.g., bleach). As used herein, "substantially free of any chlorine-based oxidants" means that the acidic detergent composition 18 comprises less than 0.01 wt % of any chlorine-based oxidant. In accordance with yet another aspect of the present invention the acidic detergent composition may further include a chelating agent. In accordance with a still further aspect of the present invention, the surfactant included in the acidic detergent may be an anionic surfactant. The surfactant could be any one of a disulfonated surfactant, a linear chain sulfonated surfactant, and a nonionic surfactant, or any two or all of a disulfonated surfactant, a linear chain sulfonated surfactant, and a nonionic surfactant. The acidic detergent composition 18 can further include other additives such as a brightener, a pH modifier, a colorant, and/or water.

In accordance with the principles of the present invention, the phosphoric acid may be present in the acidic detergent composition 18 in an amount in a range from about 30 wt % to about 70 wt %, and the surfactant may be present in the acidic detergent composition 18 in an amount in a range from about 5 to about 30 wt %. According to another embodiment, the disulfonated surfactant may be present in the acidic detergent composition 18 in an amount in a range from about 2 wt % to about 10 wt %; the linear chain sulfonated surfactant may be present in the acidic detergent composition 18 in an amount in a range from about 3 wt % to about 15 wt %; the nonionic surfactant may be present in the acidic detergent composition 18 in an amount in a range from about 0.5 wt % to about 5 wt %; and the chelating agent may be present in the acidic detergent composition 18 in an amount in the range from about 1 wt % to about 10 wt %, wherein the weight percent (wt %) is base on the total weight of the acidic detergent composition 18.

In other embodiments, the brightener may be present in the acidic detergent composition 18 in an amount in a range from about 0.01 wt % to about 3 wt %; the pH modifier may be present in the acidic detergent composition 18 in an amount in a range from about 0.2 wt % to about 5 wt %; the water may be present in the acidic detergent composition 18 in an amount in a range from about 20 wt % to about 40 wt %, wherein the wt % is base on the total weight of the acidic detergent composition 18. When present, the colorant is used in a sufficient quantity for its intended effect.

According to embodiments of the present invention, the acidic detergent composition 18 is combined with the flush liquid 16 in a sufficient quantity so as to reduce the pH of the flush solution 20 to less than 5. For example, the pH of the flush solution 20 may be in a range from about 2 to less than 5, from about 2 to about 4.5, from about 2.5 to about 4.5, or from about 3 to about 4.

The phosphoric acid used in the acidic detergent compositions 18 of the present invention is not particularly limited to any specific commercial source. According to one aspect, the phosphoric acid content of the acidic detergent composition 18 is sufficient to lower the pH of the flush solution 20 to the desired extent.

As used herein, the term "surfactant" is a compound that contains a lipophilic segment and a hydrophilic segment, which when added to water or solvents, reduces the surface tension of the system. According to an embodiment of the invention, the acidic detergent composition 18 includes a disulfonated surfactant, a linear chain sulfonated surfactant; and a nonionic surfactant. The disulfonated surfactant can be an alkyldiphenyloxide disulfonate compound, such as sodium decyl diphenyl oxide disulfonate. The linear chain sulfonated surfactant can be a linear alkylbenzene sulfonated compound, such as dodecylbenzene sulfonic acid. And the nonionic surfactant can be an ethoxylated fatty alcohol compound, such as an ethoxylated C12 to C15 alcohol compound.

As used herein, the term "chelating agent" is a multidentate ligand, which can form several bonds to a single metal ion. According to a principle of the invention, the chelating agent is capable of binding iron at the pH conditions of the flush water. For example, the chelating agent can be a phosphonobutane-tricarboxylic acid compound, such as 2-phosphonobutane 1,2,4-tricarboxylic acid.

As used herein, the terms "brightener" or "optical brightener" are chemical compounds that are used to enhance the appearance of color of the fabric materials 10. Suitable brighteners include coumarins, naphthotriazolylstilbenes, benzoxazolyl, benzimidazoyl, naphthylimide, and diaminostilbene disulfonates. For example, the brightener can be a sulfonated biphenyl distilbene, such as disodium 2,2'-(4,4'-biphenylylenedivinylene)dibenzenesulfonate.

As used herein, the term "pH modifier" is either a base or acid that is used in a sufficient quantity to provide the acidic detergent composition 18 with the appropriate level of acidity for lowering the pH of the flush solution. Accordingly, the pH modifier can be an acidic compound or a basic compound. For example, the pH modifier can be a basic compound, such as sodium hydroxide.

The water used in the acidic detergent compositions 18 of the present invention is not particularly limited to any specific source. However, the maximum residual disinfectant levels of chlorine in the water should not be in excess of the federal Environmental Protection Agency (EPA) requirements of an average maximum of 4 mg/L (ppm). Additionally, the hardness of the water should be taken into account so as to maximize the efficiency of the chelating agent to bind and sequester iron.

According to one embodiment of the present invention, the flush liquid 16 may be water. The water utilized as the flush liquid 16 of the present invention is not particularly limited to any specific source. However, the maximum residual disinfectant levels of chlorine in the water should not be in excess of the federal Environmental Protection Agency (EPA) requirements of an average maximum of 4 mg/L (ppm). Advantageously, the residual disinfectant levels of chlorine in the water are less than about 3 ppm, less than about 2 ppm, or less than about 1 ppm, for example. Additionally, the hardness of the water should be taken into account so as to maximize the efficiency of the chelating agent to bind and sequester iron, and to maximize the efficiency of the surfactants to bind and solubilize dirt and other contaminants.

While not essential for the purposes of the present invention, the non-limiting list of additional components illustrated hereinafter are suitable for use in the instant acidic detergent compositions 18 and may be desirably incorporated in certain embodiments of the invention, for example to assist or enhance cleaning performance, for treatment of the fabric materials 10 to be cleaned, or to modify the aesthetics of the acidic detergent composition 18 as is the case with perfumes, colorants, dyes or the like.

The precise nature of these additional components, and levels of incorporation thereof, will depend on the physical form of the acidic detergent composition 18 and the nature of the cleaning operation for which it is to be used. Suitable additional materials include, but are not limited to, other surfactants, other chelating agents, builders, dye transfer inhibiting agents, viscosity modifiers, dispersants, enzymes, enzyme stabilizers, catalytic materials, hydrogen peroxide, sources of hydrogen peroxide, preformed peracids, polymeric dispersing agents, threshold inhibitors for hard water precipitation pigments, clay soil removal/anti-redeposition agents, suds suppressors, fabric hueing agents, perfumes, structure elasticizing agents, fabric softeners, carriers, hydrotropes, processing aids, solvents, and mixtures thereof.

The invention will now be described, by way of embodiment, with reference to the following examples.

EXAMPLES

Exemplary acidic detergent based compositions may comprise phosphoric acid, surfactants, such as a disulfonated surfactant, a liner chain sulfonated surfactant, a nonionic surfactant, a chelating agent, a brightener, a pH modifier, and water. Accordingly, amounts of the foregoing ingredients may be advantageously present in the following amounts (wt % based on the total weight of the composition):

| | |
|---|---|
| the phosphoric acid - | about 30 wt % to about 70 wt %; |
| the disulfonated surfactant - | about 2 wt % to about 10 wt %; |
| the linear chain sulfonated surfactant - | about 3 wt % to about 15 wt %; |
| the nonionic surfactant- | about 0.5 wt % to about 5 wt %; |
| the chelating agent- | about 1 wt % to about 10 wt %; |
| the brightener- | about 0.01 wt % to about 3 wt %; |
| the pH modifier- | about 0.2 wt % to about 5 wt %; and |
| water- | about 20 wt % to about 40 wt %. |

Example 1

| | Ingredient | CAS # | Amount (wt %) |
|---|---|---|---|
| 1. | Water | 7732-18-5 | 28.5 |
| 2. | Phosphoric acid | 7664-38-2 | 50 |
| 3. | Sodium Decyl Diphenyl Oxide Disulfonate | 36445-71-3 | 5 |
| 4. | Dodecylbenzene Sulfonic Acid | 27176-87-0 | 8 |
| 5. | 2-Phosphonobutane 1,2,4 Tricarboxylic Acid | 37971-36-1 | 5.9 |
| 6. | Alcohols C12-15, Ethoxylated | 68131-39-5 | 1.25 |
| 7. | Tinopal CBS-X | 16090-02-1 | 0.025 |
| 8. | Sodium Hydroxide | 1310-73-2 | 1.31 |
| 9. | Keyacid Red GN | 67786-14-6 | 0.0005 |

An exemplary process for preparing the composition of Example 1 is to blend ingredients 1-9 in a vessel. The products will be blended in such that the consistency will be in a state of a homogeneous aqueous solution or powder, so that the composition is in the appropriate percentage range described.

By virtue of the foregoing, there is provided an acidic detergent composition and method for cleaning fabric materials contaminated with chlorhexidine or avobenzone, but without the drawbacks of associated with traditional detergent compositions or methods that cause irreversible staining of the laundry articles.

While the present invention has been illustrated by a description of particular embodiments thereof and specific examples, and while the embodiments have been described in some detail, they are not intended to restrict or in any way limit the scope of the appended claims to such detail. Additional advantages and modifications will readily appear to those skilled in the art. By way of example, the acidic detergent composition 18 could be introduced into the washing machine 14 as a solid, such as manually with a scoop into the tub 22 or first stage 24; as a liquid by pouring into the tub 22 or first stage 24, or as a liquid solution that is plumbed into the washing machine 14 wither to be mixed with the flush liquid 16 or already combined therewith. Further, although any wash or bleach cycle will likely occur after the flush cycle has completed and the flush solution 20 has been discharged, the advantages of the present invention may be accomplished by conducting the wash and/or bleach cycles without discharge of the flush solution 20. The invention in its broader aspects is therefore not limited to the specific details, representative apparatus and methods and illustrative examples shown and described. Accordingly, departures may be made from such details without departing from the scope or spirit of the general inventive concept.

Having described the invention, what is claimed is:

1. A method of cleaning fabric materials comprising loading fabric materials into a washing machine adapted to carry out separate flush, wash, and bleach cycles;

including a flush solution having a pH of less than 5 comprised of a flush liquid and an acidic detergent composition including phosphoric acid and a surfactant;

performing a flush cycle of the washing machine with the fabric materials and the flush solution whereby chlorhexidine and/or avobenzone on or in the fibers of the fabric materials are removed or eliminated therefrom; and further comprising discharging the flush solution and subsequently conducting a wash cycle with the fabric material in the washing machine.

2. The method of claim 1 wherein the washing machine includes a tub, the fabric material being loaded into the tub, the flush solution being included in the tub, and the flush cycle being conducted with the fabric material and the flush solution in the tub.

3. The method of claim 1 wherein the washing machine is a continuous batch washer having a plurality of stages, the fabric material be loaded into a first of the stages, the flush solution being included in the first stage, and the flush cycle being conducted with the fabric material and the flush solution in first stage.

4. The method of claim 3 further comprising discharging the flush solution from the first stage.

5. The method of claim 4 further comprising, after discharging the flush solution, moving the fabric material to a subsequent one of the stages and conducting a wash cycle with the fabric material in that subsequent stage.

6. The method of claim 3 further comprising, after the flush cycle, moving the fabric material to a subsequent one of the stages and conducting a wash cycle with the fabric material in that subsequent stage.

7. The method of claim 1 further comprising, after the flush cycle, conducting a wash cycle or a bleach cycle.

8. The method of claim 1 wherein including the flush solution includes introducing a flush liquid into the washing machine and introducing the acidic detergent composition into the washing machine.

9. The method of claim 1, wherein the flush solution is included at a pH of at least about 2.

10. The method of claim 1 further comprising, causing the flush solution to be at a temperature in a range from about 15° C. to about 95° C.

* * * * *